(12) United States Patent
Luo et al.

(10) Patent No.: US 11,326,096 B2
(45) Date of Patent: May 10, 2022

(54) RED LIGHT THERMALLY ACTIVATED DELAYED FLUORESCENCE MATERIAL, METHOD FOR PREPARING THE SAME, AND ORGANIC LIGHT EMITTING DIODE DEVICE

(71) Applicant: WUHAN CHINA STAR OPTOELECTRONICS SEMICONDUCTOR DISPLAY TECHNOLOGY CO., LTD., Hubei (CN)

(72) Inventors: Jiajia Luo, Hubei (CN); Lin Yang, Hubei (CN); Yamei Bai, Hubei (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 569 days.

(21) Appl. No.: 16/473,131

(22) PCT Filed: Feb. 18, 2019

(86) PCT No.: PCT/CN2019/075305
§ 371 (c)(1),
(2) Date: Jun. 24, 2019

(87) PCT Pub. No.: WO2020/124764
PCT Pub. Date: Jun. 25, 2020

(65) Prior Publication Data
US 2021/0355377 A1 Nov. 18, 2021

(30) Foreign Application Priority Data
Dec. 17, 2018 (CN) .......................... 201811539782.0

(51) Int. Cl.
*C09K 11/06* (2006.01)
*H01L 51/00* (2006.01)
(Continued)

(52) U.S. Cl.
CPC ............ *C09K 11/06* (2013.01); *C07D 471/14* (2013.01); *H01L 51/0072* (2013.01); *C09K 2211/1062* (2013.01); *H01L 51/5016* (2013.01)

(58) Field of Classification Search
CPC .............. C07D 471/14; H01L 51/0072; H01L 51/0071; H01L 51/5016; C09K 2211/1062; C09K 2211/1029; C09K 2211/1033
See application file for complete search history.

(56) References Cited

U.S. PATENT DOCUMENTS

2018/0323394 A1 11/2018 Haldi
2019/0084986 A1* 3/2019 Ye .......................... C07D 487/04

FOREIGN PATENT DOCUMENTS

CN 105503766 A 4/2016
CN 108203403 A 6/2018
(Continued)

OTHER PUBLICATIONS

Machine Translation of JP2007001879 (Year: 2007).*

*Primary Examiner* — Andrew K Bohaty
*Assistant Examiner* — Jenna N Chandhok

(57) ABSTRACT

A red light thermally activated delayed fluorescence material, a method for preparing the same, and an organic light emitting diode (OLED) device are provided. The OLED device has a luminescent material layer containing the red light thermally activated delayed fluorescence material. The red light thermally activated delayed fluorescence material has a specific molecular structure. The OLED device has a
(Continued)

maximum brightness ranging from 1300 to 1800 cd/m² and a maximum current efficiency ranging from 25 to 35 cd/A.

12 Claims, 3 Drawing Sheets

(51) Int. Cl.
*C07D 471/14* (2006.01)
*H01L 51/50* (2006.01)

(56) References Cited

FOREIGN PATENT DOCUMENTS

| | | | |
|---|---|---|---|
| CN | 108358897 A | | 8/2018 |
| JP | 2007001879 A | * | 1/2007 |

* cited by examiner

RED LIGHT THERMALLY ACTIVATED DELAYED FLUORESCENCE MATERIAL, METHOD FOR PREPARING THE SAME, AND ORGANIC LIGHT EMITTING DIODE DEVICE

FIELD OF INVENTION

The present invention relates to a red light thermally activated delayed fluorescence material, a method for preparing the same, and an organic light emitting diode (OLED) device, and more particularly, to a red light thermally activated delayed fluorescence material, a method for preparing the same and an OLED device having a high efficiency.

BACKGROUND OF INVENTION

Organic light emitting diodes (OLEDs) have advantages of active illumination without backlight, high luminous efficiency, wide viewing angles, fast response speed, large range of temperature adaptation, relatively simple production and processing technology, low driving potential, low energy consumption, light structure, and flexible display, so that the OLEDs have great application prospects and attract the attention of many researchers.

In an OLED, the most important thing is a luminescent guest material which plays a leading role. The luminescent guest material used in early OLEDs was fluorescent material. Because the ratio of singlet to triplet excitons in the OLED is 1:3, the theoretical internal quantum efficiency (IQE) of the OLED based on fluorescent materials can only reach 25%, which greatly limits the application of the fluorescent electroluminescent device. Another luminescent guest material is a heavy metal complex phosphorescent material which can utilize both of excitons of the singlet exited state and the triplet exited state due to its spin-orbit interaction of the heavy atoms so that the IQE can reach 100% in theory. However, the phosphorescence-based material usually requires the precious metals such as Ir, and Pt. In red light material, the heavy metal complex phosphorescent material needs a breakthrough. Other luminescent guest material such as pure organic thermally activated delayed fluorescence (TADF) material which has a designated molecular structure to allow triplet excited excitons to return to the singlet excited state through reverse intersystem crossing (RISC) and then radiation transition back to the ground state to illuminate thereby the singlet and triplet excitions can be utilized at the same time and the IQE can also reach 100%.

For TADF materials, a fast reverse intersystem crossing constant (kRISC) and a high photoluminescence quantum yield (PLQY) are necessary for the preparation of high efficiency OLEDs. At present, TADF materials with the above requirements are still a minority compared to heavy metal Ir complex materials. In the field of red light where phosphorescent heavy metal materials need a breakthrough, TADF materials are more fewer.

It is therefore necessary to provide a red light thermally activated delayed fluorescence material and an organic light emitting diode device in order to solve the problems existing in the conventional technology as described above.

SUMMARY OF INVENTION

The primary object of the present invention is to provide a red light thermally activated delayed fluorescence material and a method for preparing the same. The red light thermally activated delayed fluorescence material has excellent luminescent properties, which comprises an electron donor (D) portion combined with an electron acceptor (A) portion and the electron donating ability of the electron donor portion can be increased by using different substituents, so that the red light thermally activated delayed fluorescence material has very low singlet triplet energy state to achieve red light emitting.

Another object of the present invention is to provide an organic light emitting diode device comprising a luminescent material layer formed by the abovementioned red light thermally activated delayed fluorescence material.

To achieve above objects, one embodiment of the present invention provides a red light thermally activated delayed fluorescence material, having a structural formula (I) as follows:

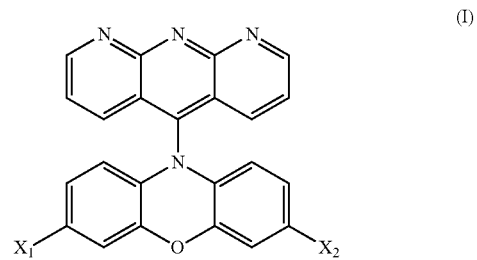

wherein $X_1$ and $X_2$ are independently selected from the group consisting of isobutyl, methoxyl, and dimethylamino group.

In one embodiment of the present invention, the red light thermally activated delayed fluorescence material is

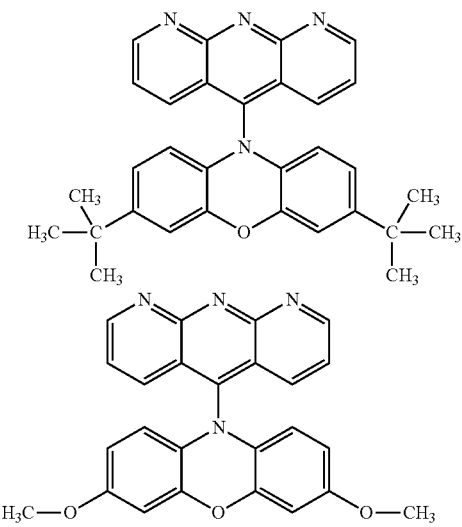

or

-continued

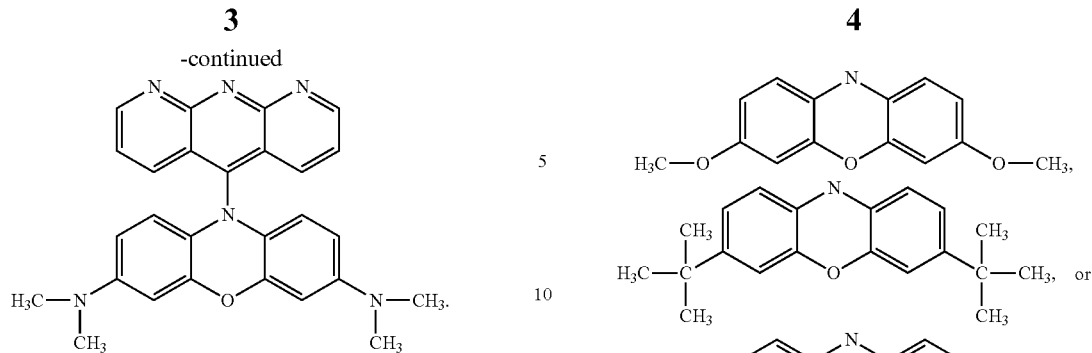

Another embodiment of the present invention provides a method for preparing a red light thermally activated delayed fluorescence material, comprising steps of: (1) adding a first reactant and a second reactant into a reaction container, wherein the first reactant has a molecular structure as following formula (A) and the second reactant has a molecular structure as following formula (B):

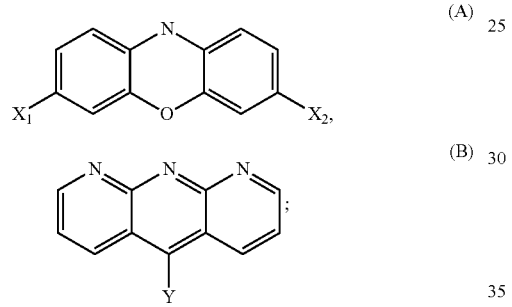

(2) adding palladium acetate, tri-tert-butylphosphine tetrafluoroborate, sodium tert-butoxide, and toluene into the reaction container; and (3) heating the reaction container under an inert gas at a temperature higher than 120° C. to produce a red light thermally activated delayed fluorescence material, wherein the red light thermally activated delayed fluorescence material has a structural formula (I) as follows:

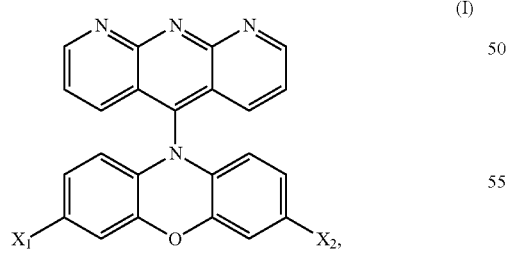

wherein Y is F, Cl, or Br; and $X_1$ and $X_2$ are independently selected from the group consisting of isobutyl, methoxyl, and dimethylamino group.

In one embodiment of the present invention, the inert gas is argon.

In one embodiment of the present invention, the first reactant is

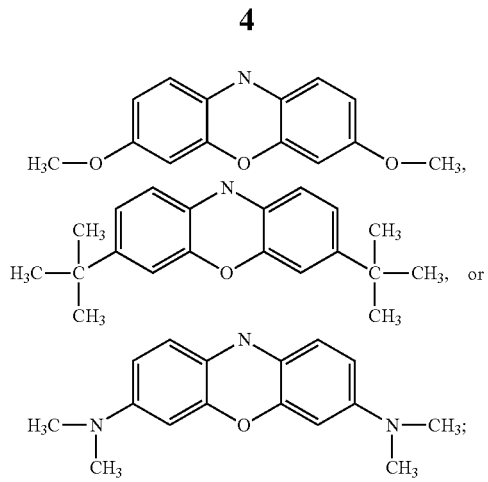

and the second reactant is

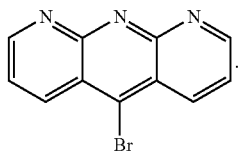

In one embodiment of the present invention, the red light thermally activated delayed fluorescence material is

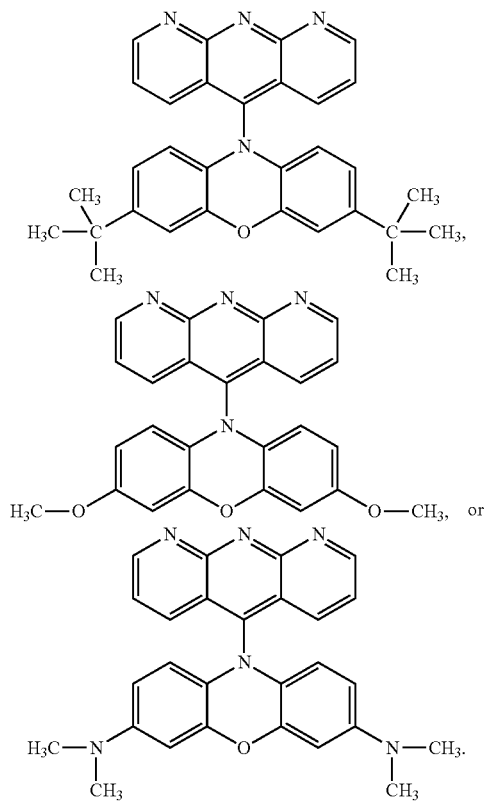

A further embodiment of the present invention provides an n organic light emitting diode (OLED) device, comprising: a transparent substrate; a transparent conductive layer disposed on the transparent substrate; a hole transport layer disposed on the transparent conductive layer; a luminescent material layer disposed on the hole transport layer; an electron transport layer disposed on the luminescent material layer; and a cathode layer disposed on the electron transport layer, wherein the luminescent material layer comprises a red light thermally activated delayed fluorescence material as described above.

In one embodiment of the present invention, the transparent conductive layer is indium tin oxide.

In one embodiment of the present invention, the hole transport layer is poly(3,4-ethylenedioxythiophene):poly(styrenesulfonate) (PEDOT:PSS).

In one embodiment of the present invention, the electron transport layer is 1,3,5-tri[(3-pyridyl)-phen-3-yl]benzene, 1,3,5-tris(1-phenyl-1H-benzimidazole-2-yl)benzene, or 3,3'-[5'-[3-(3-pyridinyl)phenyl][1,1':3',1''-terphenyl]-3,3''-diyl]bispyridine.

In one embodiment of the present invention, the luminescent material layer has a thickness ranging from 15 to 20 nm.

In one embodiment of the present invention, the hole transport layer has a thickness ranging from 40 to 50 nm.

In one embodiment of the present invention, the electron transport layer has a thickness ranging from 30 to 40 nm.

In one embodiment of the present invention, the OLED device has a maximum brightness ranging from 1300 to 1800 cd/m$^2$.

In one embodiment of the present invention, the OLED device has a maximum current efficiency ranging from 25 to 35 cd/A.

DETAILED DESCRIPTION OF PREFERRED EMBODIMENTS

The detailed description of the following embodiments is used for exemplifying the specific embodiments of the present invention by referring to the accompany drawings. Furthermore, directional terms described by the present invention, such as upper, lower, front, back, left, right, inner, outer, side, etc., are only directions by referring to the accompanying drawings, and thus the directional terms are used to describe and understand the present invention, but the present invention is not limited thereto.

The present invention provides a red light thermally activated delayed fluorescence material, having a structural formula (I) as follows:

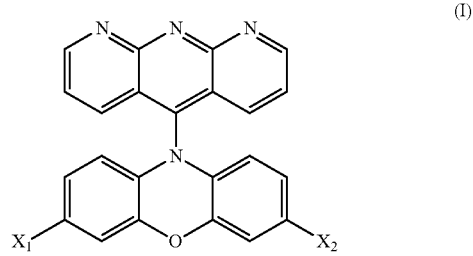

(I)

wherein $X_1$ and $X_2$ are independently selected from the group consisting of isobutyl, methoxyl, and dimethylamino group.

A method for preparing the red light thermally activated delayed fluorescence material, comprising steps of: (S1) adding a first reactant and a second reactant into a reaction container, wherein the first reactant has a molecular structure as following formula (A) and the second reactant has a molecular structure as following formula (B):

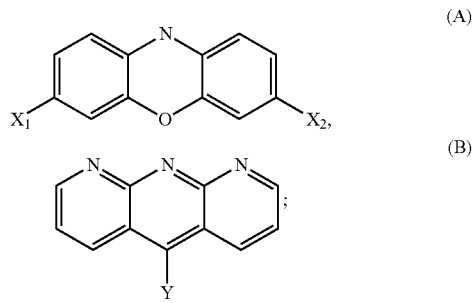

(A)

(B)

(S2) adding palladium acetate, tri-tert-butylphosphine tetrafluoroborate, sodium tert-butoxide, and toluene into the reaction container; and (S3) heating the reaction container under an inert gas at a temperature higher than 120° C. to produce a red light thermally activated delayed fluorescence material, wherein the red light thermally activated delayed fluorescence material has a structural formula (I) as follows:

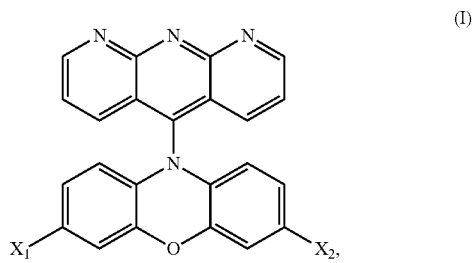

(I)

wherein Y is F, Cl, or Br; and $X_1$ and $X_2$ are independently selected from the group consisting of isobutyl, methoxyl, and dimethylamino group. In this embodiment, the inert gas is argon ($Ar_2$).

Figure 1:
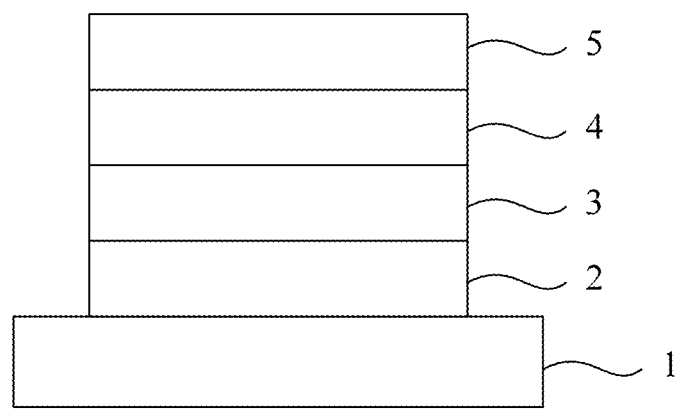
FIG. 1 is a schematic view of an organic light emitting diode device according to one embodiment of the present invention.

Referring to FIG. 1, which shows a schematic view of an organic light emitting diode (OLED) device according to one embodiment of the present invention. The OLED device mainly comprises a transparent conductive substrate 1 formed by a transparent substrate and a transparent conductive layer, a hole transport layer 2, a luminescent material layer 3, an electron transport layer 4, and a cathode layer 5. The transparent conductive layer is disposed on the transparent substrate, the transparent conductive layer can be an indium tin oxide (ITO) electrode, but it is not limited thereto. A transparent electrode generally known in the art is applicable. Preferably, the hole transport layer 2 can be Poly(3,4-ethylenedioxythiophene):poly(styrenesulfonate) (PEDOT:PSS), but it is not limited thereto. Preferably, the hole transport layer 2 has a thickness less than 50 nm, and the thickness is preferably 40 to 50 nm. For example, the thickness is 50, 45, or 40 nm, but it is not limited thereto.

In one embodiment of the present invention, the luminescent material layer 3 comprises a red light thermally activated delayed fluorescence material having a molecular structure as follows:

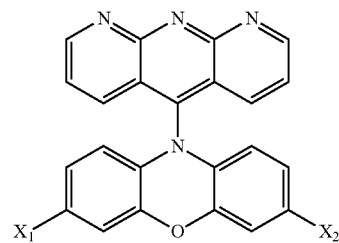

wherein $X_1$ and $X_2$ are independently selected from the group consisting of isobutyl (—C(CH$_3$)$_3$), methoxyl (—OCH$_3$), and dimethylamino group (—N(CH$_3$)$_2$).

Preferably, the red light thermally activated delayed fluorescence material has a specific structure as following formulas (1) to (3):

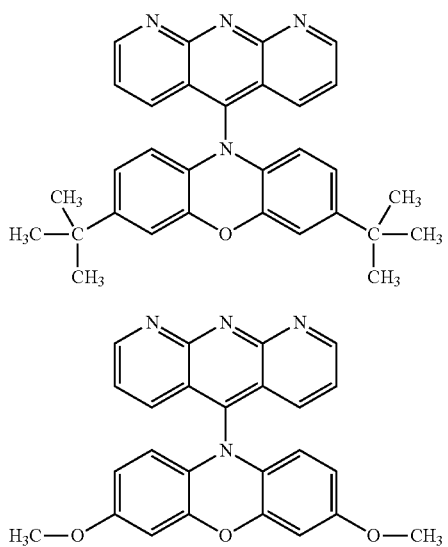

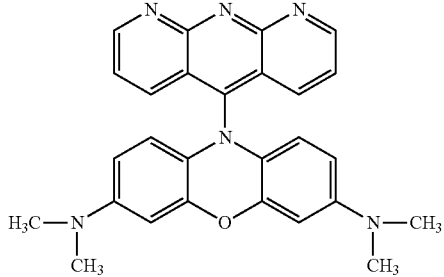

The synthetic route and synthetic steps of the formula (1) are as follows:

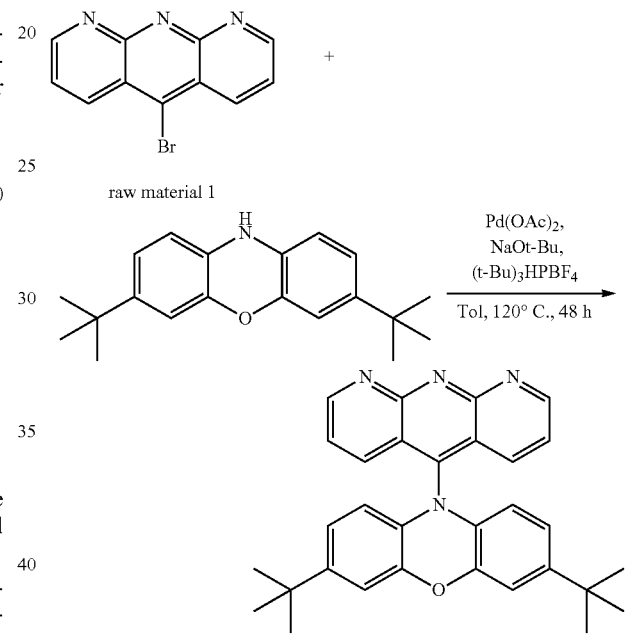

Adding a raw material 1 (1.29 g, 5 mmol), 3,6-di-(tert-butyl)phenoxazine (1.77 g, 6 mmol), palladium acetate (45 mg, 0.2 mmol), and tri-tert-butylphosphine tetrafluoroborate (0.17 g, 0.6 mmol) into 100 ml two-neck bottle, and then adding NaOt-Bu (0.58 g, 6 mmol) into the two-neck bottle in the glove box. Next, 40 ml of a dehydrated and oxygen-removed toluene is injected in an argon atmosphere. The reaction is carried out for 48 hours under 120° C. Next, pouring the reaction solution into 200 ml ice water after being cooled to room temperature, and extracting by dichloromethane for 3 times, and combining collected organic phases, followed by being purified and isolated with a silica gel by a column chromatography (dichloromethane:hexane, v:v, 1:2) to obtain 2.1 g powder with red color and yield 89%. $^1$H NMR (300 MHz, CD$_2$Cl$_2$, δ): 8.70 (d, J=6.3 Hz, 2H), 8.39 (d, J=6.9 Hz, 2H), 7.41 (t, J=7.2 Hz, 2H), 7.00 (s, 2H), 6.82-6.78 (m, 4H), 1.27 (s, 18H). MS (EI) m/z: [M]$^+$ calcd for C$_{31}$H$_{30}$N$_4$O, 474.24; found, 474.19. Anal. Calcd for C$_{31}$H$_{30}$N$_4$O: C, 78.45, H, 6.39, N, 11.81; found: C, 78.37, H, 6.27, N, 11.62.

The synthetic route and synthetic steps of the formula (2) are as follows:

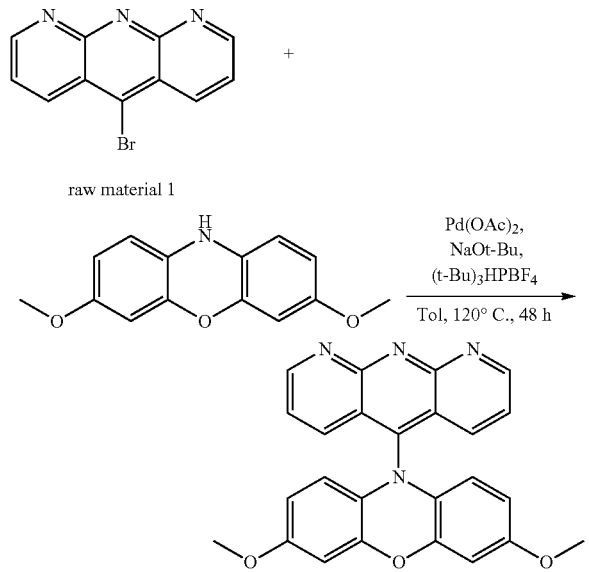

raw material 1

Adding a raw material 1 (1.29 g, 5 mmol), 3,6-di-(methoxyl)phenoxazine (1.46 g, 6 mmol), palladium acetate (45 mg, 0.2 mmol), and tri-tert-butylphosphine tetrafluoroborate (0.17 g, 0.6 mmol) into 100 ml two-neck bottle, and then adding NaOt-Bu (0.58 g, 6 mmol) into the two-neck bottle in the glove box. Next, 40 ml of a dehydrated and oxygen-removed toluene is injected in an argon atmosphere. The reaction is carried out for 48 hours under 120° C. Next, pouring the reaction solution into 200 ml ice water after being cooled to room temperature, and extracting by dichloromethane for 3 times, and combining collected organic phases, followed by being purified and isolated with a silica gel by a column chromatography (dichloromethane:hexane, v:v, 1:2) to obtain 1.9 g powder with red color and yield 90%. $^1$H NMR (300 MHz, CD$_2$Cl$_2$, δ): 8.70 (d, J=6.3 Hz, 2H), 8.39 (d, J=6.9 Hz, 2H), 7.41 (t, J=7.2 Hz, 2H), 6.57 (s, 2H), 6.51-6.43 (m, 4H), 3.84 (s, 6H). MS (EI) m/z: [M]$^+$ calcd for C$_{25}$H$_{18}$N$_4$O$_3$, 422.14; found, 422.10. Anal. Calcd for C$_{25}$H$_{18}$N$_4$O$_3$: C, 71.08, H, 4.30, N, 13.26; found: C, 71.00, H, 4.27, N, 12.92.

The synthetic route and synthetic steps of the formula (3) are as follows:

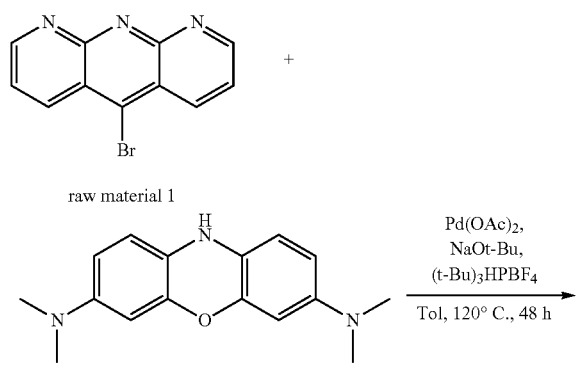

raw material 1

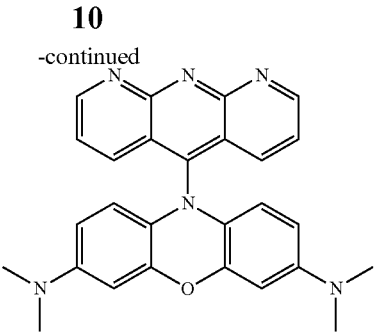

Adding a raw material 1 (1.29 g, 5 mmol), 3,6-di-(N,N'-dimethyl)phenoxazine (1.61 g, 6 mmol), palladium acetate (45 mg, 0.2 mmol), and tri-tert-butylphosphine tetrafluoroborate (0.17 g, 0.6 mmol) into 100 ml two-neck bottle, and then adding NaOt-Bu (0.58 g, 0.6 mmol) into the two-neck bottle in the glove box. Next, 40 ml of a dehydrated and oxygen-removed toluene is injected in an argon atmosphere. The reaction is carried out for 48 hours under 120° C. Next, pouring the reaction solution into 200 ml ice water after being cooled to room temperature, and extracting by dichloromethane for 3 times, and combining collected organic phases, followed by being purified and isolated with a silica gel by a column chromatography (dichloromethane:hexane, v:v, 1:2) to obtain 1.7 g powder with red color and yield 76%. $^1$H NMR (300 MHz, CD$_2$Cl$_2$, δ): 8.70 (d, J=6.3 Hz, 2H), 8.39 (d, J=6.9 Hz, 2H), 7.41 (t, J=7.2 Hz, 2H), 6.52-6.48 (m, 4H), 4.37 (s, 2H), 2.90 (s, 12H). MS (EI) m/z: [M]$^+$ calcd for C$_{27}$H$_{24}$N$_6$O, 448.20 found, 448.19. Anal. Calcd for C$_{27}$H$_{24}$N$_6$O: C, 72.30, H, 5.39, N, 18.74; found: C, 72.17, H, 5.27, N, 18.62.

The electrochemical energy level of the above formula (1) to formula (3) are shown in below Table 1.

TABLE 1

| | PL Peak (nm) | S$_1$ (eV) | T$_1$ (eV) | ☐E$_{ST}$ (eV) | HOMO (eV) | LUMO (eV) |
|---|---|---|---|---|---|---|
| Formula (1) | 609 | 2.04 | 2.00 | 0.04 | −5.35 | −2.23 |
| Formula (2) | 616 | 2.01 | 1.93 | 0.08 | −5.65 | −2.24 |
| Formula (3) | 627 | 1.98 | 1.91 | 0.07 | −5.62 | −2.23 |

Figure 2:
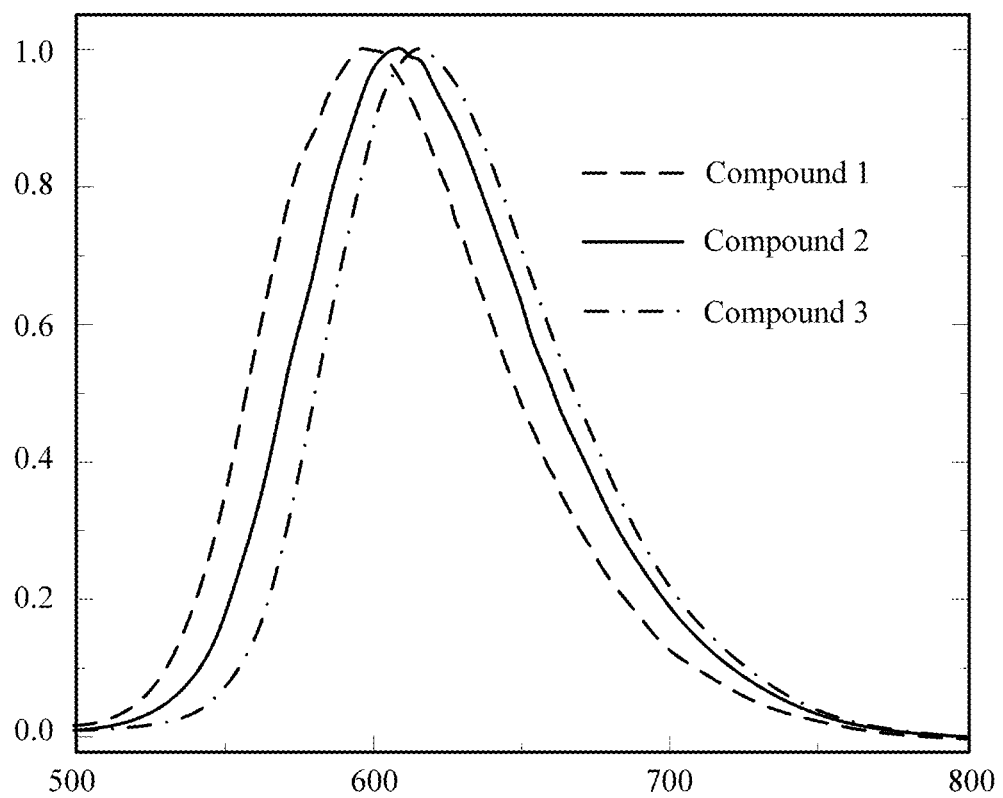
FIG. 2 is a photoluminescence spectrum of the red light thermally activated delayed fluorescence material (compound 1-3) in toluene solution under room temperature according to the present invention.

Referring to FIG. 2, which shows a photoluminescence spectrum of the red light thermally activated delayed fluorescence material as abovementioned formula 1-3 in toluene solution under room temperature.

Figure 3:
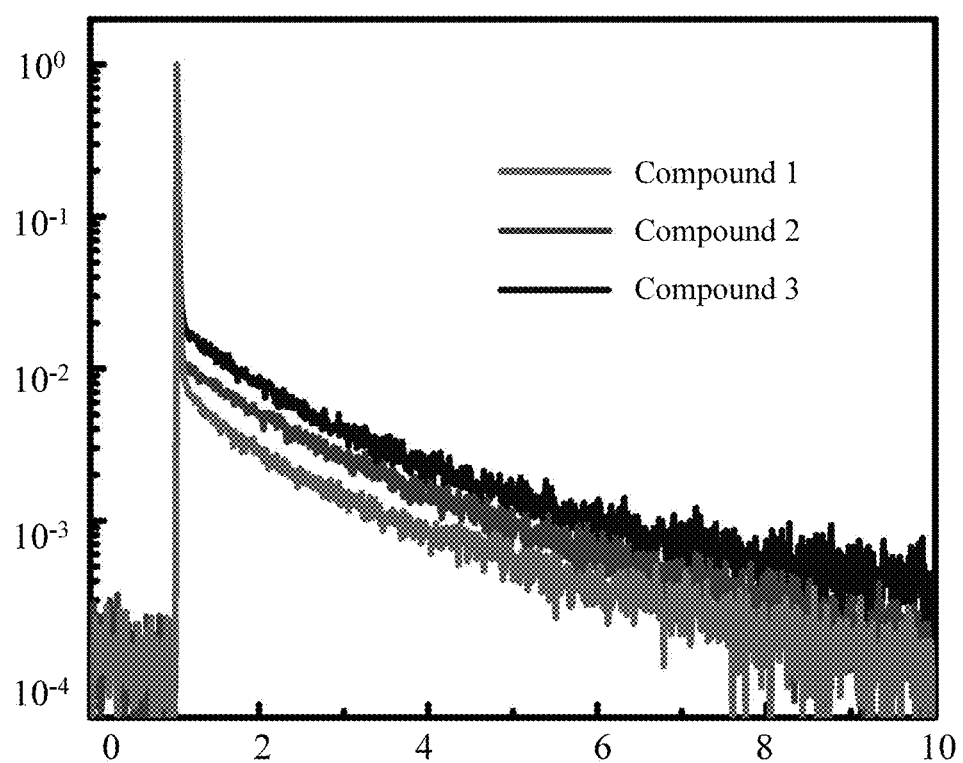
FIG. 3 is a transient photoluminescence spectrum of the red light thermally activated delayed fluorescence material (compound 1-3) in toluene solution under room temperature according to the present invention.

Referring to FIG. 3, which shows a transient photoluminescence spectrum of the red light thermally activated delayed fluorescence material as abovementioned formula 1-3 in toluene solution under room temperature.

In one embodiment, the luminescent material layer 3 has a thickness less than 20 nm, and it is preferably 15 to 20 nm. For example, the thickness can be 15, 17, or 20 nm, but it is not limited thereto.

Preferably, the electron transport layer 4 is 1,3,5-tri[(3-pyridyl)-phen-3-yl]benzene (Tm$_3$PyPB), 1,3,5-tris(1-phenyl-1H-benzimidazole-2-yl)benzene (TPBI), or 3,3'-[5'-[3-(3-pyridinyl)phenyl][1,1': 3',1"-terphenyl]-3,3"-diyl] bispyridine (TmPyPB). The electron transport layer 4 has a thickness less than 40 nm, and it is preferably 30 to 40 nm. For example, the thickness can be 30, 35, or 40 nm, but it is not limited thereto.

In one embodiment of the present invention, the OLED device has a maximum brightness ranging from 1300 to 1800 cd/m² (candle power/square meter), and more preferably the maximum brightness is 1465-1587 cd/m². Preferably, the OLED device has a maximum current efficiency ranging from 25 to 35 cd/A (candle power/ampere), and preferably the maximum current efficiency is 27.3-29.1 cd/A.

The red light thermally activated delayed fluorescence material provided in the above formula (1) to formula (3) is applicable to be a luminescent material layer to produce an organic light emitting diode device. The specific method includes: spin-coating PESOT:PSS on a cleaned conductive glass (ITO) substrate, and then sequentially performing evaporation of the red light thermally activated delayed fluorescence material of the present invention, Tm₃PyPB, 1 nm LiF, and 100 nm Al under a high vacuum condition. The devices A1 to A3 as shown in below Table 2 can be obtained.

TABLE 2

| | |
|---|---|
| A1 | ITO/PEDOT:PSS (50 nm)/formula (1) (3% 20 nm)/Tm₃PyPB (40 nm)/LiF (1 nm)/Al (100 nm) |
| A2 | ITO/PEDOT:PSS (50 nm)/formula (2) (3% 20 nm)/Tm₃PyPB (40 nm)/LiF(1 nm)/Al (100 nm) |
| A3 | ITO/PEDOT:PSS (50 nm)/formula (3) (3% 20 nm)/Tm₃PyPB (40 nm)/LiF(1 nm)/Al (100 nm) |

Further, performance of the above devices A1 to A3 are measured, in which the properties of current-brightness-petential of the devices are measured by Keithley source measurement system with a calibrated silicon photodiode (Keithley 2400 Sourcemeter, Keithley 2000 Currentmeter) and the electroluminescence spectrum is measure by French company JP SPEX CCD3000 spectrometer. All measurements were performed at room temperature in the atmosphere. The performance data of the devices are shown in below Table 3.

TABLE 3

| device | maximum brightness(cd/m²) | maximum current efficiency(cd/A) | CIEx | maximum external quantum efficiency(%) |
|---|---|---|---|---|
| A1 | 1465 | 28.6 | 0.62 | 19.3 |
| A2 | 1564 | 27.3 | 0.63 | 18.7 |
| A3 | 1587 | 29.1 | 0.63 | 21.6 |

From Table 3, in the OLED devices produced by the red light thermally activated delayed fluorescence material of formulas (1) to (3) provided in the present invention, the device A3 has a maximum brightness of 1587 cd/m², a maximum current efficiency of 29.1 cd/A, and a maximum external quantum efficiency of 21.6%.

The present application has been described by the above related embodiments, but the above embodiments are merely examples for implementing the present application. It must be noted that the disclosed embodiments do not limit the scope of the present application. Rather, modifications and equivalent arrangements included in the spirit and scope of the claims are intended to be included within the scope of the present application.

What is claimed is:

1. A red light thermally activated delayed fluorescence material, having a structural formula (I) as follows:

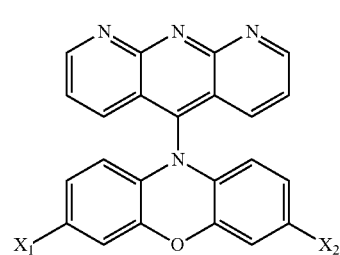

(I)

wherein $X_1$ and $X_2$ are independently selected from the group consisting of isobutyl, methoxyl, and dimethylamino group.

2. The red light thermally activated delayed fluorescence material according to claim 1, wherein the red light thermally activated delayed fluorescence material is

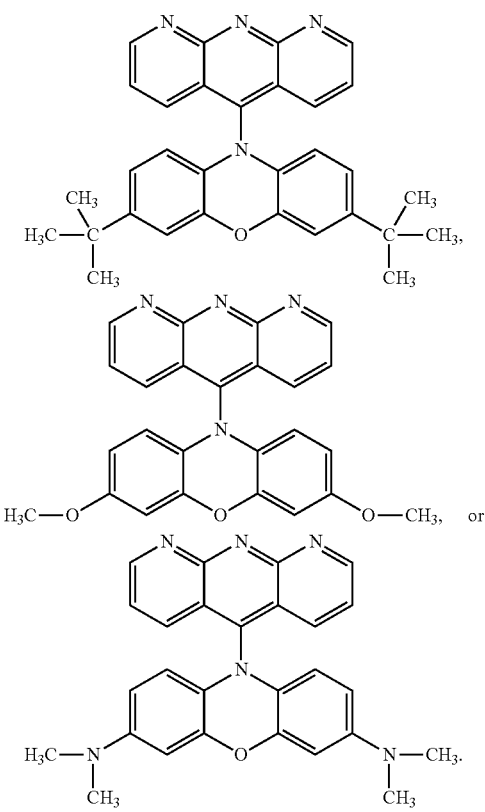

3. An organic light emitting diode (OLED) device, comprising:
a transparent substrate;
a transparent conductive layer disposed on the transparent substrate;
a hole transport layer disposed on the transparent conductive layer;
a luminescent material layer disposed on the hole transport layer;
an electron transport layer disposed on the luminescent material layer; and
a cathode layer disposed on the electron transport layer, wherein the luminescent material layer comprises a red light thermally activated delayed fluorescence material according to claim 1.

4. The OLED device according to claim 3, wherein the transparent conductive layer is indium tin oxide.

5. The OLED device according to claim 3, wherein the hole transport layer is poly(3,4-ethylenedioxythiophene):poly(styrenesulfonate).

6. The OLED device according to claim 3, wherein the electron transport layer is 1,3,5-tri[(3-pyridyl)-phen-3-yl]benzene, 1,3,5-tris(1-phenyl-1H-benzimidazole-2-yl)benzene, or 3,3'-[5'-[3-(3-pyridinyl)phenyl][1,1':3',1"-terphenyl]-3,3"-diyl]bispyridine.

7. The OLED device according to claim 3, wherein the luminescent material layer has a thickness ranging from 15 to 20 nm; the hole transport layer has a thickness ranging from 40 to 50 nm; and the electron transport layer has a thickness ranging from 30 to 40 nm.

8. The OLED device according to claim 3, wherein the OLED device has a maximum brightness ranging from 1300 to 1800 cd/m² and a maximum current efficiency ranging from 25 to 35 cd/A.

9. A method for preparing a red light thermally activated delayed fluorescence material, comprising steps of:

adding a first reactant and a second reactant into a reaction container, wherein the first reactant has a molecular structure as following formula (A) and the second reactant has a molecular structure as following formula (B):

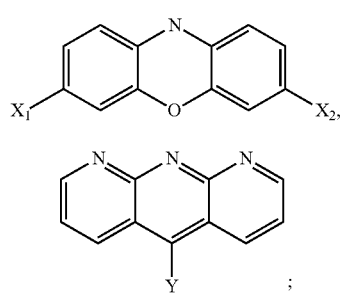

adding palladium acetate, tri-tert-butylphosphine tetrafluoroborate, sodium tert-butoxide, and toluene into the reaction container; and heating the reaction container under an inert gas at a temperature higher than 120° C. to produce a red light thermally activated delayed fluorescence material, wherein the red light thermally activated delayed fluorescence material has a structural formula (I) as follows:

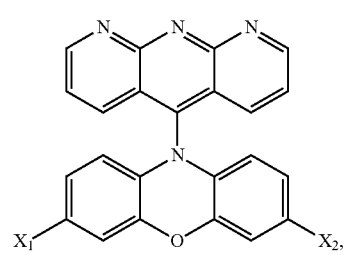

wherein Y is F, Cl, or Br; and $X_1$ and $X_2$ are independently selected from the group consisting of isobutyl, methoxyl, and dimethylamino group.

10. The method according to claim 9, wherein the inert gas is argon.

11. The method according to claim 9, wherein the first reactant is

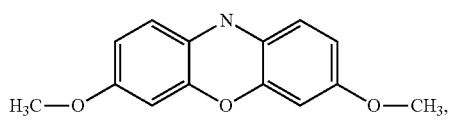

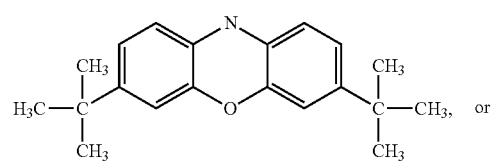

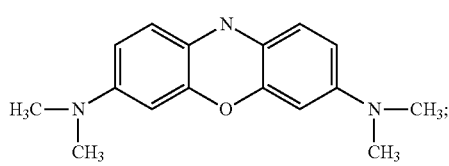

and the second reactant is

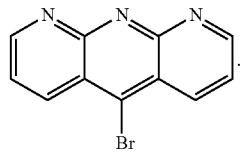 [SMILES: Brc1c2cccnc2nc2ncccc12]

12. The method according to claim 9, wherein the red light thermally activated delayed fluorescence material is

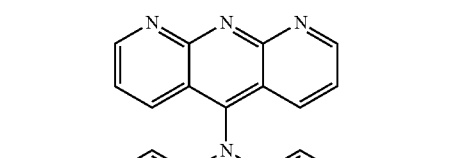

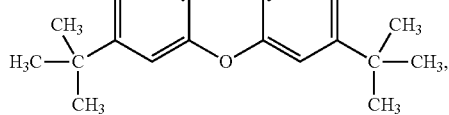

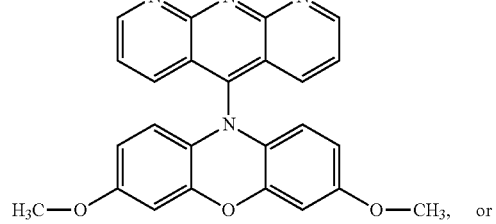

-continued
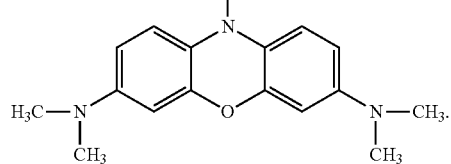
* * * * *